US012685820B2

(12) United States Patent
Petit et al.

(10) Patent No.: US 12,685,820 B2
(45) Date of Patent: Jul. 21, 2026

(54) AUTOINJECTOR HOUSING

(71) Applicant: Becton Dickinson France, Le Pont-de-Claix (FR)

(72) Inventors: Louis Petit, Venon (FR); Pierre Ducarouge, Milan (IT); Michael Fiard, Corenc (FR); Matthieu Charvin, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 801 days.

(21) Appl. No.: 17/924,184

(22) PCT Filed: May 19, 2021

(86) PCT No.: PCT/EP2021/063330
§ 371 (c)(1),
(2) Date: Nov. 9, 2022

(87) PCT Pub. No.: WO2021/234020
PCT Pub. Date: Nov. 25, 2021

(65) Prior Publication Data
US 2023/0173181 A1      Jun. 8, 2023

(30) Foreign Application Priority Data

May 20, 2020    (EP) ..................................... 20305534

(51) Int. Cl.
*A61M 5/20*         (2006.01)
*A61M 5/315*        (2006.01)
(Continued)

(52) U.S. Cl.
CPC .......... *A61M 5/20* (2013.01); *A61M 5/31591* (2013.01); *A61M 5/322* (2013.01); *A61M 5/50* (2013.01)

(58) Field of Classification Search
CPC .......... A61M 5/20; A61M 5/322; A61M 5/50; A61M 5/2033; A61M 5/326;
(Continued)

(56) References Cited

U.S. PATENT DOCUMENTS 6,494,863 B1 * 12/2002 Shaw .................. A61M 5/5013
604/110
9,486,582 B2    11/2016 Abry et al.
(Continued)

FOREIGN PATENT DOCUMENTS

CN          103313742 B      11/2015
CN          107362036 A      11/2017
(Continued)

*Primary Examiner* — Courtney D Heinle
*Assistant Examiner* — Andrew Thanh Bui
(74) *Attorney, Agent, or Firm* — The Webb Law Firm

(57) ABSTRACT

Provided herein is a housing assembly for a drug delivery device, including a first housing part having a first proximal end comprising a first engagement portion and a second engagement portion, a first distal end, and a first sidewall therebetween defining a first longitudinal axis and a first interior, the first sidewall comprising one or more windows therethrough; and a second housing part having a second proximal end, a second distal end comprising a third engagement portion and a fourth engagement portion, and a second sidewall therebetween defining a second longitudinal axis and a second interior.

15 Claims, 5 Drawing Sheets

(51) Int. Cl.
    *A61M 5/32*          (2006.01)
    *A61M 5/50*          (2006.01)

(58) Field of Classification Search
    CPC .. A61M 2005/2073; A61M 2005/2013; A61M
                    2205/581; A61M 2205/582; A61M
                    5/3204; A61M 2005/206
    See application file for complete search history.

(56)             References Cited

U.S. PATENT DOCUMENTS

| | | | |
|---|---|---|---|
| 9,616,174 | B2 | 4/2017 | Fabien et al. |
| 9,662,447 | B2 | 5/2017 | Fabien et al. |
| 9,707,343 | B2 | 7/2017 | Fabien et al. |
| 9,707,357 | B2 | 7/2017 | Fabien et al. |
| 9,717,851 | B2 | 8/2017 | Fabien et al. |
| 9,731,075 | B2 | 8/2017 | Jugl et al. |
| 9,821,115 | B2 | 11/2017 | Wozencraft |
| 10,653,838 | B2 | 5/2020 | Fabien et al. |
| 10,744,264 | B2 | 8/2020 | Saussaye et al. |
| 10,799,647 | B2 | 10/2020 | Hostettler et al. |
| 10,881,795 | B2 | 1/2021 | Giambattista |
| 10,994,080 | B2 * | 5/2021 | Young ................. A61M 5/2033 |
| 11,305,062 | B2 | 4/2022 | Fabien et al. |
| 2009/0254043 | A1 | 10/2009 | Van Bulow et al. |
| 2013/0313823 | A1 | 11/2013 | Holmqvist |
| 2015/0231333 | A1 * | 8/2015 | Lannan ................... A61M 5/50 |
| | | | 604/198 |
| 2017/0165428 | A1 | 6/2017 | Sall |
| 2019/0134315 | A1 | 5/2019 | Moser et al. |
| 2019/0240421 | A1 | 8/2019 | Brasington |
| 2022/0176044 | A1 * | 6/2022 | Zhang .................... A61M 5/34 |

FOREIGN PATENT DOCUMENTS

| | | |
|---|---|---|
| CN | 107743405 B | 8/2020 |
| CN | 110520175 B | 3/2022 |
| EP | 3622987 A1 | 3/2020 |
| JP | 2009540986 A | 11/2009 |
| JP | 2014519917 A | 8/2014 |
| RU | 182223 U1 | 8/2018 |
| WO | 2008003560 A1 | 1/2008 |
| WO | 2016193627 A1 | 12/2016 |
| WO | 2017051113 A1 | 3/2017 |
| WO | 2017081422 A1 | 5/2017 |

* cited by examiner

132

132

170

160

172

166

164

AUTOINJECTOR HOUSING

CROSS REFERENCE TO RELATED APPLICATIONS

This application is the United States national phase of International Application No. PCT/EP2021/063330 filed May 19, 2021, and claims priority to European Patent Application No. 20305534.8 filed May 20, 2020, the entire disclosures of which are hereby incorporated by reference in their entirety.

BACKGROUND OF THE INVENTION

Field of the Invention

The present disclosure relates generally to drug delivery devices and, more specifically, to single-use autoinjector housings with improved torque and dismantling resistance.

Description of Related Art

Automatic drug delivery devices, such as autoinjectors, are often designed to be single-use devices. Such devices are often shipped as multiple components to a drug supplier, who will provide a pre-filled syringe (PFS) of a given medicament. Once the PFS is introduced into the devices, the devices are then assembled for delivery to patients. For increased safety of such single-use devices, for example, to prevent a user from exposing themselves to the needle or a glass PFS that could break, it is desirable to include certain features making it more difficult to dismantle an assembled autoinjector. Accordingly, a need exists in the art for a multi-component housing for a drug delivery device that, once assembled, is resistant to dismantling.

SUMMARY OF THE INVENTION

Provided herein is a housing assembly for a drug delivery device, including a first housing part, the first housing part having a first proximal end comprising a first engagement portion and a second engagement portion, a first distal end, and a first sidewall therebetween defining a first longitudinal axis and a first interior, the first sidewall comprising one or more windows therethrough, and a second housing part, the second housing part having a second proximal end, a second distal end comprising a third engagement portion and a fourth engagement portion, and a second sidewall therebetween defining a second longitudinal axis and a second interior, wherein the first engagement portion forms a lock with the third engagement portion, thereby joining the first housing part and the second housing part such that the first longitudinal axis and the second longitudinal axis are coaxial, and wherein, when the first housing part and the second housing part are joined, the second engagement portion abuts the fourth engagement portion, such that the first housing part cannot rotate relative to the second housing part.

Also provided herein is an injection device including a housing assembly, the housing assembly including a first housing part, the first housing part having a first proximal end comprising a first engagement portion and a second engagement portion, a first distal end, and a first sidewall therebetween defining a first longitudinal axis and a first interior, the first sidewall comprising one or more windows therethrough, and a second housing part, the second housing part having a second proximal end, a second distal end comprising a third engagement portion and a fourth engagement portion, and a second sidewall therebetween defining a second longitudinal axis and a second interior, wherein the first engagement portion forms a lock with the third engagement portion, thereby joining the first housing part and the second housing part such that the first longitudinal axis and the second longitudinal axis are coaxial, and wherein, when the first housing part and the second housing part are joined, the second engagement portion abuts the fourth engagement portion, such that the first housing part cannot rotate relative to the second housing part. The injection device further includes a syringe comprising a reservoir and a needle in fluid communication therewith, the syringe received within the first interior and/or the second interior, and a driver received within the second interior and configured to, upon actuation, expel medicament from the reservoir through the needle.

Clause 1. In accordance with a configuration of the present application a housing assembly for a drug delivery device includes a first housing part having a first proximal end having a first engagement portion and a second engagement portion, a first distal end, and a first sidewall therebetween defining a first longitudinal axis and a first interior. The first sidewall includes one or more windows therethrough. The housing assembly also includes a second housing part having a second proximal end, a second distal end comprising a third engagement portion and a fourth engagement portion, and a second sidewall therebetween defining a second longitudinal axis and a second interior. The first engagement portion forms a lock with the third engagement portion, thereby joining the first housing part and the second housing part such that the first longitudinal axis and the second longitudinal axis are coaxial. When the first housing part and the second housing part are joined, the second engagement portion abuts the fourth engagement portion, such that the first housing part cannot rotate relative to the second housing part.

Clause 2. The housing assembly of clause 1, wherein the first distal end includes an opening.

Clause 3. The housing assembly of any of clauses 1-2, wherein the first distal end includes a moveable needle shield including a sidewall having proximal and distal ends, the needle shield including an opening at the distal end thereof and being slidable relative to the first housing part.

Clause 4. The housing assembly of any of clauses 1-3, wherein the first engagement portion and the third engagement portion form a positive lock.

Clause 5. The housing assembly of any of clauses 1-4, wherein the first engagement portion and the third engagement portion form an irreversible lock.

Clause 6. The housing assembly of any of clauses 1-5, wherein the first engagement portion comprises a resiliently-biased flexible clip including a radially-outward extending protrusion.

Clause 7. The housing assembly of clause 6, wherein the radially-outward extending protrusion includes a first beam and a second beam spaced apart from the first beam, the second beam extending substantially parallel to the first beam along the first longitudinal axis.

Clause 8. The housing assembly of clause 7, wherein the first and second beam include an insertion contact surface that extends radially outward from proximal to distal ends thereof along the first longitudinal axis, and a removal contact surface longitudinally spaced from and angled with respect to the insertion contact surface.

Clause 9. The housing assembly of any of clauses 6-8, wherein the resiliently-biased flexible clip is deflected radially inward from an initial biased position as the insertion contact surface engages the third engagement portion.

Clause 10. The housing assembly of clause 9, wherein, when the first housing part and the second housing part are joined, the resiliently-biased clip returns to the initial biased position.

Clause 11. The housing assembly of any of clauses 6-10, wherein, when the first housing part and the second housing part are joined, the removal contact surface and the third engagement portion prevent separation of the first housing part and the second housing part.

Clause 12. The housing assembly of any of clauses 6-11, wherein the radially-outward extending protrusion is received within the third engagement portion.

Clause 13. The housing assembly of any of clauses 1-12, wherein the third engagement portion is a recess in the second sidewall.

Clause 14. The housing assembly of any of clauses 1-13, wherein the third engagement portion is an opening in the second sidewall.

Clause 15. The housing assembly of any of clauses 1-14, wherein the second engagement portion and the fourth engagement portion comprise circumferentially-arranged contact surfaces in the first sidewall and the second sidewall, respectively.

Clause 16. The housing assembly of any of clauses 1-15, wherein the second engagement portion includes one or more walls of the window.

Clause 17. The housing assembly of any of clauses 1-16, wherein the second engagement portion and the fourth engagement portion includes one or more steps in the first sidewall and the second sidewall, respectively.

Clause 18. The housing assembly of any of clauses 1-17, wherein the fourth engagement portion includes a u-shaped recess configured to receive the first proximal end therein.

Clause 19. The housing assembly of clause 18, wherein the u-shaped recess receives at least a portion of the window therein.

Clause 20. An injection device including the housing assembly of any of clauses 1-19, also including a syringe having a reservoir and a needle in fluid communication therewith, the syringe received within the first interior and/or the second interior, and a driver received within the second interior and configured to, upon actuation, expel medicament from the reservoir through the needle.

DESCRIPTION OF THE INVENTION

Figure 1:
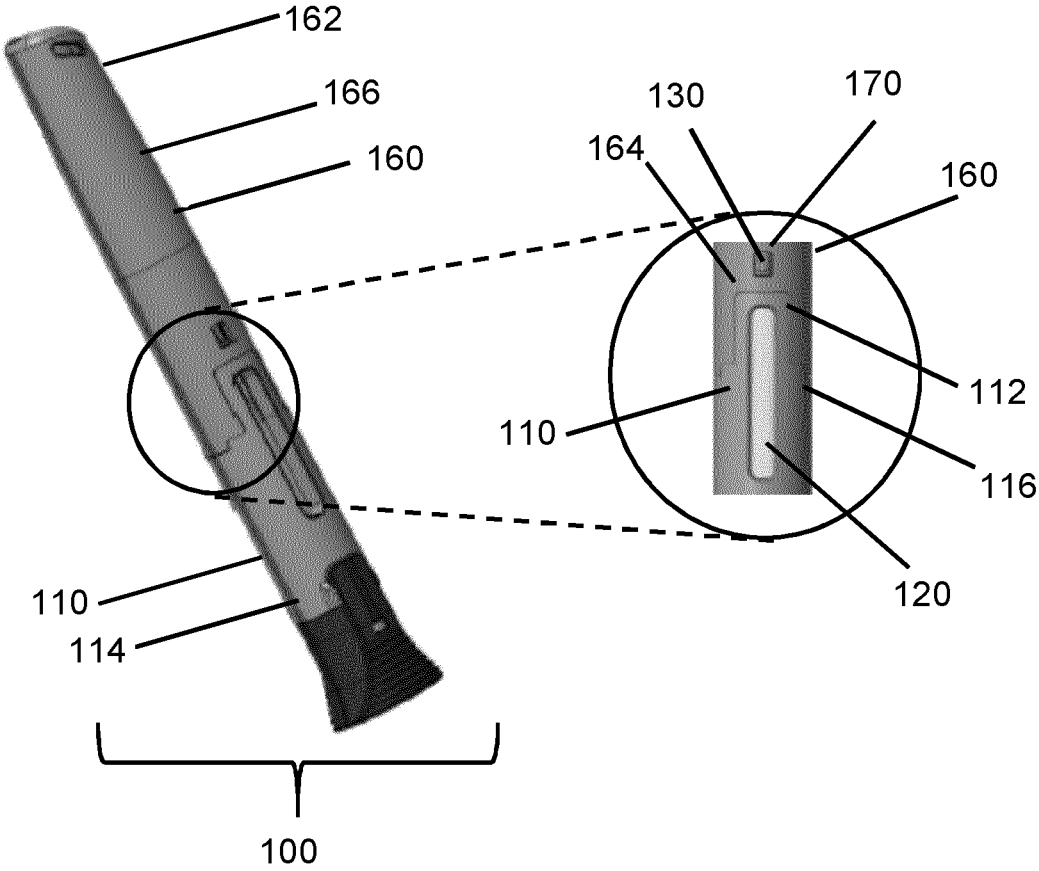
FIG. 1 is a perspective view, including a magnified view, of a housing assembly according to a non-limiting embodiment or aspect.
Figure 2:
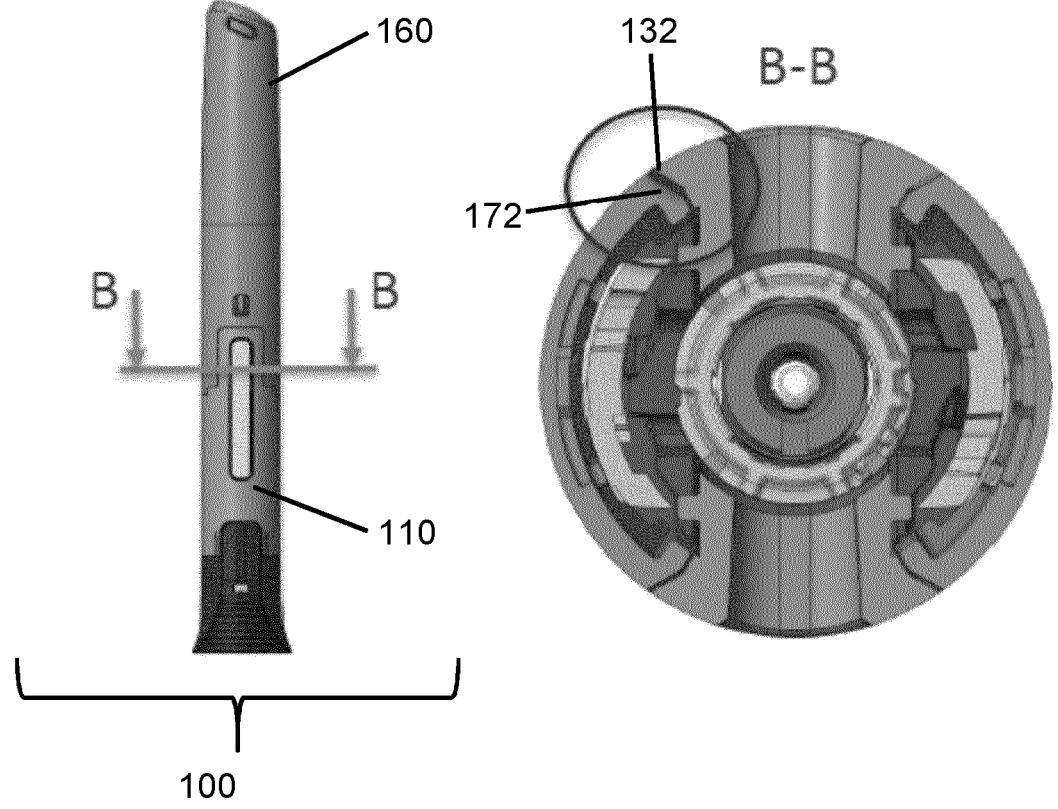
FIG. 2 is a side view, including a cross-section through plane B-B, of a housing assembly according to a non-limiting embodiment or aspect.
Figure 3:
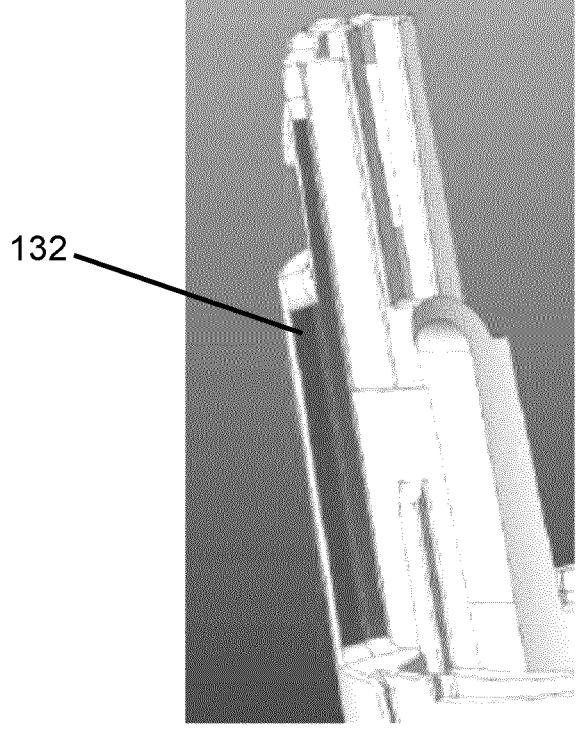
FIG. 3 is a perspective view of a housing assembly according to a non-limiting embodiment or aspect.
Figure 4:
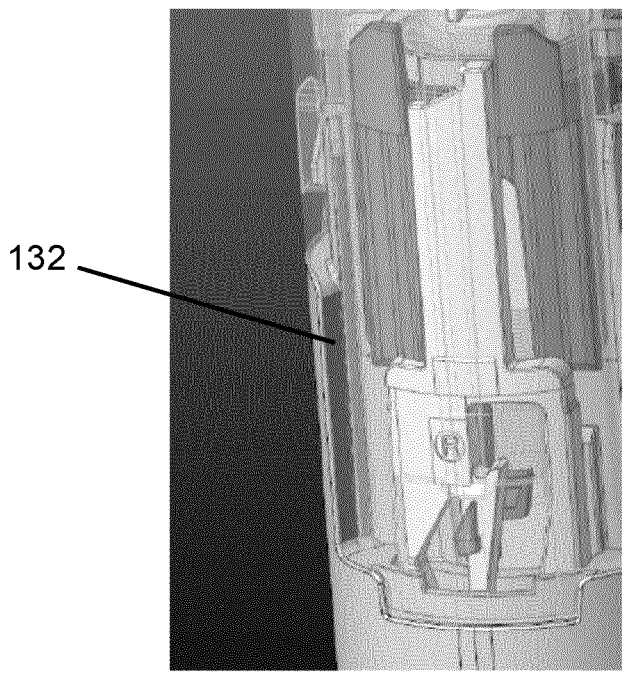
FIG. 4 is a perspective view of a housing assembly according to a non-limiting embodiment or aspect.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Provided herein is a housing assembly for a drug delivery device. As used herein, a "drug delivery device" encompasses autoinjectors, pen injectors, safety syringes, and the like. Non-limiting examples of drug delivery devices for which the presently-described housing assembly may be useful are disclosed in, for example and without limitation, U.S. Pat. Nos. 9,616,174; 9,662,447; 9,707,343; 9,707,357; 9,717,851; 9,486,582; and International Patent Application Publication Nos. WO 2016/193627; WO 2017/051113; and WO 2017/081422, the disclosures of which are hereby incorporated by reference in their entirety. The housing assembly described herein is advantageous in that it provides excellent resistance to dismantling, such that a patient or other user of the drug delivery device is unlikely to inadvertently dismantle the device through normal handling, thus the risk of exposure to sharps or glass cartridges is minimized. In addition, the configuration of the housing portion provides an optimal surface for application of indicia to the outer surface of the drug delivery device when the device is assembled.

Turning to FIG. 1, shown is a drug delivery device 100 having a housing assembly including a first housing part 110 and a second housing part 160. The first housing part 110 has a first proximal end 112, a first distal end 114, and a first sidewall 116 therebetween defining a first longitudinal axis and an interior for holding at least a portion of a syringe (not shown). In non-limiting embodiments or aspects, first housing part 110 includes at least one window 120 such that the interior, including optionally at least a portion of a syringe, is visible. In non-limiting embodiments or aspects, window 120 is formed of glass, plastic, or any other clear or substantially clear material. In non-limiting embodiments or aspects, window 120 is wholly contained within first housing part 110 (e.g., first sidewall 116 forms the perimeter of window 120). Second housing part 160 has second proximal end 162, second distal end 164, and second sidewall 166 therebetween, defining a second longitudinal axis and an interior for holding at least a portion of a syringe (not shown). First housing part 110 and second housing part 160 can be formed of any suitable material known to those of skill in the art, such as plastic.

First housing portion 110 can include an opening at first distal end 114 thereof (not shown), which can allow a needle of a syringe provided in the interior of the housing to access an injection site, either by virtue of movement of the syringe and/or needle within the housing assembly or retraction of a needle shield. To this end, in non-limiting embodiments or aspects, first housing portion 110 can include a needle shield (not shown). In non-limiting embodiments or aspects, needle shield can be a moveable needle shield, slidable relative to first housing part 110. In non-limiting embodiments or aspects, needle shield is a telescoping needle shield, slidable on an outside surface of first housing part 110 or an inside surface of first housing part 110.

First housing part 110 includes at first proximal end 112 thereof a first engagement portion 130 and a second engagement portion (not shown in FIG. 1). Second housing part 160 includes at distal end 164 thereof, a third engagement portion 170, and a fourth engagement portion (not shown in FIG. 1). First engagement portion 130 of first housing part 110 can form a lock with third engagement portion 170 of second housing part 160. In non-limiting embodiments or aspects, the lock formed between first engagement portion 130 of first housing part 110 and third engagement portion 170 of second housing part 160 is a positive lock. In non-limiting embodiments or aspects, the lock formed between first engagement portion 130 of first housing part 110 and third engagement portion 170 of second housing part 160 is an irreversible lock, such that first housing part 110 and second housing part 160 cannot be pulled axially away from one another. In non-limiting embodiments or aspects, when first housing part 110 and second housing part 160 are joined and a lock is formed between first engagement portion 130 of first housing part 110 and third engagement portion 170 of second housing part 160, the first longitudinal axis of first housing part 110 and second longitudinal axis of second housing part 160 are coaxial.

With reference to FIGS. 2-5, previously-referenced second engagement portion 132 at first proximal end 112 of first housing part 110 and fourth engagement portion 172 at second distal end 164 of second housing part 160 are shown. In non-limiting embodiments or aspects, when first housing part 110 and second housing part 160 are joined, second engagement portion 132 of first housing part 110 and fourth engagement portion 172 of second housing part 160 abut, such that first housing part 110 and second housing part 160 cannot be rotated relative to one another. In non-limiting embodiments or aspects, second engagement portion 132 and/or fourth engagement portion 172 are formed in first sidewall 116 and second sidewall 166, respectively. In non-limiting embodiments or aspects, the second engagement portion 132 is at least a portion of a wall forming a perimeter of window 120. In non-limiting embodiments or aspects, fourth engagement portion 172 is a u-shaped recess configured to receive first proximal end 112, including at least a portion of window 120, therein. In non-limiting embodiments or aspects, second engagement portion 132 and/or fourth engagement portion 172 include one or more steps, such that interaction of second engagement portion 132 and fourth engagement portion 172 involves abutment of two or more longitudinally and/or circumferentially-offset surfaces (for example, as shown in FIG. 1).

Figure 5:
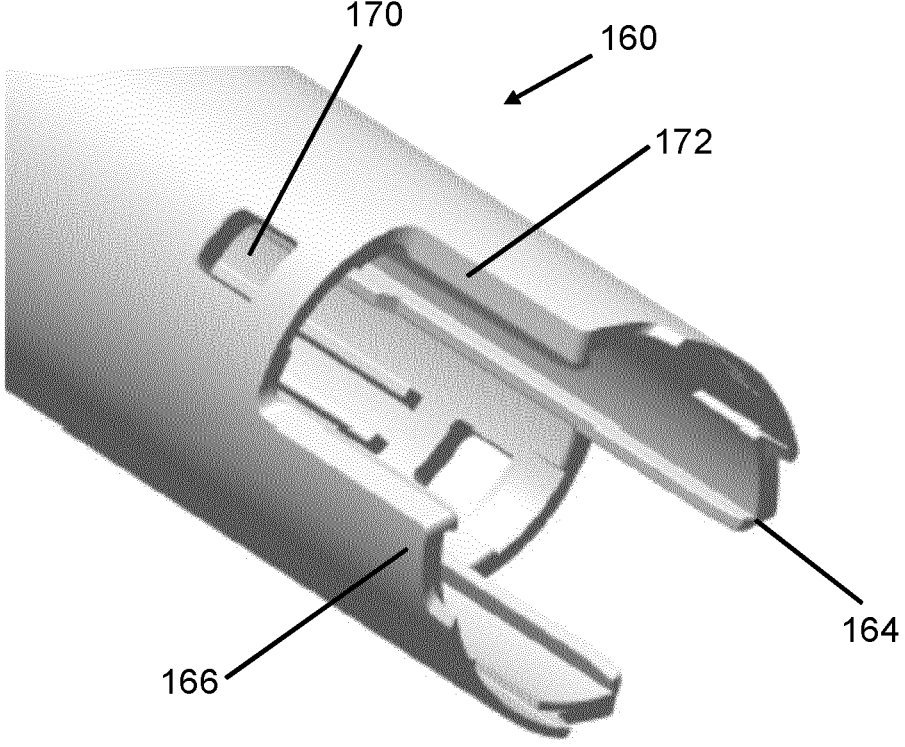
FIG. 5 is a perspective view of a housing assembly according to a non-limiting embodiment or aspect.
Figure 6A:
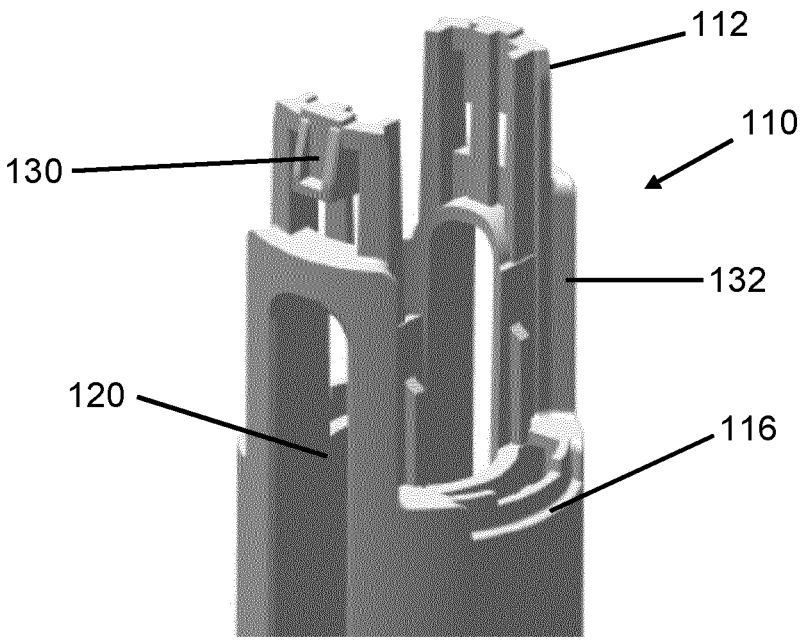
FIGS. 6A and 6B are perspective views of a housing assembly according to a non-limiting embodiment or aspect.
Figure 6B:
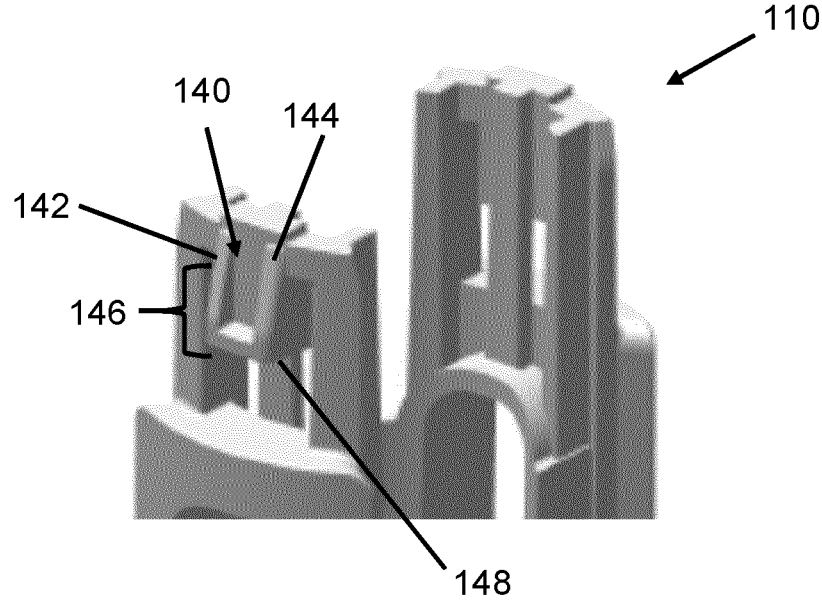

With reference to FIGS. 5, 6A, and 6B, embodiments and aspects of first and third engagement portions 130, 170 are shown. FIG. 5 shows an embodiment or aspect of third engagement portion 170 in which third engagement portion 170 is an opening in second sidewall 166. In other non-limiting embodiments or aspects, third engagement portion 170 is a recess in an interior surface of second sidewall 166. FIGS. 6A and 6B show embodiments or first engagement portion 130. In non-limiting embodiments or aspects, first engagement portion 130 is a resiliently-biased clip. In non-limiting embodiments or aspects, first engagement portion 130 is a resiliently-biased, flexible clip. In non-limiting embodiments or aspects, first engagement portion 130 is a resiliently-biased, flexible clip having a radially-outward extending protrusion 140.

With further reference to FIG. 6B, in non-limiting embodiments or aspects, first engagement portion 130 is a resiliently-biased, flexible clip having a radially-outward extending protrusion 140, protrusion 140 including first beam 142 and second beam 144. In non-limiting embodiments or aspects, first beam 142 and second beam 144 extend parallel or substantially parallel to one another along first longitudinal axis defined by first sidewall 116. In non-limiting embodiments or aspects, protrusion 140 includes insertion contact surface 146 formed by at least a portion of first beam 142 and second beam 144. In non-limiting embodiments or aspects, contact surface 146 extends radially along first longitudinal axis, such that insertion contact surface 146 is angled radially inward (not shown) or outward (shown) with respect to longitudinal axis defined by first sidewall 116.

In non-limiting embodiments or aspects, as first housing portion 110 and second housing portion 160 are joined, insertion contact surface 146 interacts with an interior surface of second sidewall 166, optionally flexing protrusion 140 inward, until third engagement portion 170, in the illustrated embodiment of FIG. 5 an opening in second sidewall 166, passes insertion contact surface 146, at which point resiliently-biased protrusion 140 returns to its biased position and protrusion 140 is received within third engagement portion 170. While not illustrated, those of skill in the art will appreciate that the converse, where insertion contact surface 146 interacts with an exterior surface of second sidewall 166, flexing protrusion radially outward, falls within the scope of the present disclosure.

With continuing reference to FIG. 6B, in non-limiting embodiments or aspects, protrusion 140 includes removal contact surface 148. In non-limiting embodiments or aspects, removal contact surface 148 is perpendicular to first longitudinal axis defined by first sidewall 116. In non-limiting embodiments or aspects, removal contact surface 148 interacts with a perpendicularly-arranged (relative to second longitudinal axis of second housing portion 160) surface of third engagement portion 170, such that first housing portion 110 and second housing portion 160 are joined, removal contact surface 148 abuts third removal portion 170, and first housing portion 110 and second housing portion 160 cannot be pulled axially away from one another.

The invention enables to increase torsion dismantling force, traction dismantling force and flexion dismantling force between the first and the second housing portion. The arrangement of first 130 and third 170 engagement portions and second 132 and fourth 172 engagement portions provides acceptable resistance to dismantling, falling within specifications for each type of force.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A housing assembly for a drug delivery device, comprising:

a first housing part comprising:

a first proximal end comprising a first engagement portion comprising a resiliently-biased clip comprising a radially-outward extending protrusion, and a second engagement portion, a first distal end, and a first sidewall therebetween defining a first longitudinal axis and a first interior, the first sidewall comprising one or more windows therethrough; and a second housing part comprising:

a second proximal end, a second distal end comprising a third engagement portion and a fourth engagement portion, and a second sidewall therebetween defining a second longitudinal axis and a second interior, wherein the third engagement portion comprises an opening within and surrounded by the second sidewall, wherein, when the first housing part is connected to the second housing part, the first engagement portion is biased such that the radially-outward extending protrusion is received within the third engagement portion, thereby forming a positive lock with the third engagement portion and joining the first housing part and the second housing part such that the first longitudinal axis and the second longitudinal axis are coaxial, and wherein, when the first housing part and the second housing part are joined, the second engagement portion abuts the fourth engagement portion, such that the first housing part cannot rotate relative to the second housing part.

2. The housing assembly of claim 1, wherein the first distal end comprises an opening.

3. The housing assembly of claim 1, wherein the first distal end comprises a moveable needle shield comprising a sidewall having proximal and distal ends, the needle shield comprising an opening at the distal end thereof and being slidable relative to the first housing part.

4. The housing assembly claim 1, wherein the first engagement portion and the third engagement portion form an irreversible lock.

5. The housing assembly of claim 1, wherein the radially-outward extending protrusion comprises a first beam and a second beam spaced apart from the first beam, the second beam extending substantially parallel to the first beam along the first longitudinal axis.

6. The housing assembly of claim 5, wherein the first and second beam comprise:

an insertion contact surface that extends radially outward from proximal to distal ends thereof along the first longitudinal axis; and a removal contact surface longitudinally spaced from and angled with respect to the insertion contact surface.

7. The housing assembly of claim 1, wherein the resiliently-biased flexible clip is deflected radially inward from an initial biased position as the insertion contact surface engages the third engagement portion.

8. The housing assembly of claim 7, wherein, when the first housing part and the second housing part are joined, the resiliently-biased clip returns to the initial biased position.

9. The housing assembly of claim 6, wherein, when the first housing part and the second housing part are joined, the removal contact surface and the third engagement portion prevent separation of the first housing part and the second housing part.

10. The housing assembly of claim 1, wherein the second engagement portion and the fourth engagement portion comprise circumferentially-arranged contact surfaces in the first sidewall and the second sidewall, respectively.

11. The housing assembly of claim 1, wherein the second engagement portion comprises one or more walls of the window.

12. The housing assembly of claim 1, wherein the second engagement portion and the fourth engagement portion comprise one or more steps in the first sidewall and the second sidewall, respectively.

13. The housing assembly of claim 1, wherein the fourth engagement portion comprises a u-shaped recess configured to receive the first proximal end therein.

14. The housing assembly of claim 13, wherein the u-shaped recess receives at least a portion of the window therein.

15. An injection device comprising:

a housing assembly comprising:

a first housing part comprising:

a first proximal end comprising a first engagement portion comprising a resiliently-biased clip comprising a radially-outward extending outward protrusion, and a second engagement portion, a first distal end, and a first sidewall therebetween defining a first longitudinal axis and a first interior, the first sidewall comprising one or more windows therethrough; and a second housing part comprising:

a second proximal end, a second distal end comprising a third engagement portion and a fourth engagement portion, and a second sidewall therebetween defining a second longitudinal axis and a second interior, wherein the third engagement portion comprises an opening within and surrounded by the second sidewall, wherein, when the first housing part and the second housing part are joined, the first engagement portion is biased such that the radially-outward extending protrusion is received within the third engagement portion, thereby forming a positive lock with the third engagement portion and joining the first housing part and the second housing part such that the first longitudinal axis and the second longitudinal axis are coaxial, and wherein, when the first housing part and the second housing part are joined, the second engagement portion abuts the fourth engagement portion, such that the first housing part cannot rotate relative to the second housing part;

a syringe comprising a reservoir and a needle in fluid communication therewith, the syringe received within the first interior and/or the second interior; and a driver received within the second interior and configured to, upon actuation, expel medicament from the reservoir through the needle.

* * * * *